United States Patent [19]

Urban

[11] Patent Number: 5,089,637

[45] Date of Patent: Feb. 18, 1992

[54] PROCESS AND INTERMEDIATES FOR 2R-BENZYL-CHROMAN-6-CARBALDEHYDE

[75] Inventor: Frank J. Urban, Groton, Conn.

[73] Assignee: Pfizer Inc., New York, N.Y.

[21] Appl. No.: 496,737

[22] Filed: Mar. 21, 1990

[51] Int. Cl.$^5$ .................................... C07D 311/58
[52] U.S. Cl. .................................. 549/407; 549/398
[58] Field of Search ............................ 549/407, 398

[56] References Cited

PUBLICATIONS

Chem. Abst., 109: 170,552t (1988).
Chem. Abst., 109: 92,718k (1988).
Chem. Abst. 108: 167,322s (1988).
Chem. Abst., 106: 67,298d (1987).
Chem. Abst., 103: 32,0762 (1985).
Chem. Abst., 97: 162,066f (1982).

*Primary Examiner*—Nicky Chan
*Attorney, Agent, or Firm*—Peter C. Richardson; J. Trevor Lumb; D. Stuart McFarlin

[57] ABSTRACT

Optically active ($C_1$–$C_3$) alkyl 2R-chroman-2-carboxylates are prepared by partial hydrolysis of the corresponding racemic ester using a microbial lipase as catalyst. Said 2R-chromancarboxylate is converted via novel 2R-(hydroxymethyl) chroman, 2R-(trifluoromethylsulfonyloxymethyl) chroman and 2R-benzylchroman intermediates into 2R-benzylchroman-6-carbaldehyde, a compound of known utility in the manufacture of certain hypoglycemic agents.

3 Claims, No Drawings

PROCESS AND INTERMEDIATES FOR 2R-BENZYL-CHROMAN-6-CARBALDEHYDE

BACKGROUND OF THE INVENTION

The present invention is directed to a process for the preparation of optically active $(C_1-C_3)$alkyl 2R-chroman-2-carboxylates via the partial enzymatic hydrolysis of the corresponding racemic ester using a microbial lipase derived from *Pseudomonas fluoroescens*. The present invention is further directed to intermediates and a multistep process for converting said 2R-chroman-2-carboxylate to 2R-benzylchroman-6-carbaldehyde, a known compound of known utility as an intermediate in the manufacture of the known hypoglycemic agent of the formula

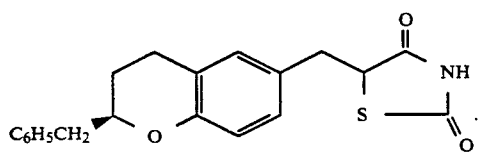

(See Eggler et al., U.S. Pat. No. 4,703,052 for details).

Optically active chroman-2-carboxylic acids and corresponding alkyl esters are generally known compounds; for example, see Schaaf et al., J. Med. Chem., v. 26, pp. 328-334 (1983). Lipase mediated resolution of some structurally related hydroxylated chroman-2-carboxylates have been recently reported in published European patent application no. 325,954.

The chemical nomenclature used herein is generally that of Rigaudy et al., IUPAC Nomenclature of Organic Chemistry, 1979 Edition, Pergammon Press, New York. An alternative name for chroman,

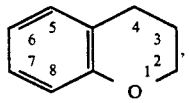

is (2H)-3,4-dihydro-1-benzopyran. An alternative name for chromene,

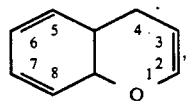

is (4H)-1-benzopyran.

SUMMARY OF THE INVENTION

The present invention is directed to a simple and high yield process for the preparation of an optically active $(C_1-C_3)$alkyl 2R-chroman-2-carboxylate which comprises the steps of:

(a) partial hydrolysis of a corresponding racemic $(C_1-C_3)$alkyl chroman-2-carboxylate (I) in a reaction-inert solvent comprising water in the presence of a catalytic amount of a microbial lipase (derived from *Pseudomonas fluorescens*) to form a mixture comprising said $(C_1-C_3)$alkyl 2R-chroman-2-carboxylate (II) and 2S-chroman-2-carboxylic acid (III); and (b) separation of said $(C_1-C_3)$alkyl 2R-chroman-2-carboxylate from said mixture.

Step (a) is depicted as follows:

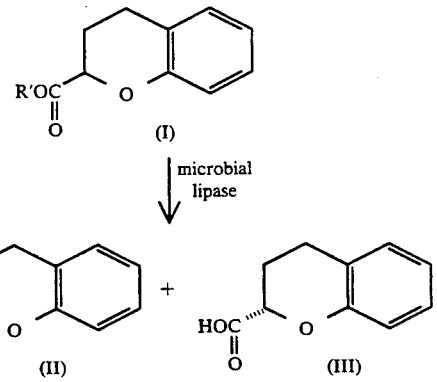

wherein R' is $(C_1-C_3)$alkyl, preferably ethyl.

The present invention is further directed to above process steps (a) and (b) further comprising the steps:

(c) hydride reduction of said $(C_1-C_3)$alkyl 2R-chroman-2-carboxylate (II) to form 2R-(hydroxymethyl)-chroman (IV, R=CH$_2$OH);

(d) reaction of said 2R-(hydroxymethyl)chroman with triflic anhydride to form 2R-(trifluoromethylsulfonyloxymethyl)chroman (IV, R=CH$_2$OSO$_2$CF$_3$);

(e) reaction of said 2R-(trifluoromethylsulfonyloxymethyl)chroman with phenylmagnesium bromide in the presence of a catalytic amount of cuprous bromide to form 2R-benzylchroman (IV, R=benzyl); and (f) formylation of said 2R-benzylchroman with N-methylformanilide in the presence of phosphorous oxychloride to form 2R-benzylchroman-2-carbaldehyde (V).

Compounds (IV) and (V) are depicted as follows:

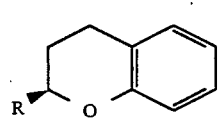

wherein R is CH$_2$OH, CH$_2$OSO$_2$CF$_3$ or benzyl; and

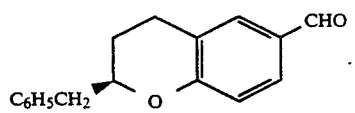

The present invention is also directed to the optically active compounds of the above formula (IV).

The expression "reaction-inert solvent comprising water" refers to a solvent system which does not interact with starting material, reagents, intermediates or product in a manner which adversely affects the yield of the desired product, which includes but is not limited to water alone.

Optionally added solvents include water miscible solvents such as R'OH or acetone, or water immiscible solvents such as toluene. Generally, alcoholic solvents other than R'OH, where R' corresponds to the alkyl group of (I) and (II), and ester solvents such as ethyl acetate are avoided, since they will generally complicate the desired partial hydrolysis of the chroman ester (I). The preferred method employs only water as solvent.

DETAILED DESCRIPTION OF THE INVENTION

The present invention provides an advantageous method for the preparation of optically active ($C_1$-$C_3$)alkyl 2R-chroman-2-carboxylates of the formula (II) depicted above. According to this process, a racemic ($C_1$-$C_3$)alkyl chroman-2-carboxylate is contacted with a catalytic amount of microbial lipase (e.g., the microbial lipase derived from *Pseudomonas fluorescens*, which is available commercially) in a reaction-inert solvent comprising water (as noted above). Reaction temperatures in the range of about 25°–40° C. are generally satisfactory, with the preferred temperature range being about 34°–37°. If the temperature is too low, the reaction will not proceed at a reasonable rate. If the temperature is too high, the enzyme, which is a protein, can be denatured and so inactivated. The preferred pH range for the reaction is about 5.5–7.3, the pH of the nascent enzyme being close to 7.

Since hydrolysis of the ester (which is neutral) leads to formation of an acid, base must be added to maintain the desired pH during hydrolysis. Dilute NaOH (e.g., 1N) is particularly well-suited for this purpose. However, it will be obvious to those skilled in the art that other bases can be substituted therefor. Measuring the amount of base required to maintain near neutral pH provides an extremely simple method for monitoring the hydrolysis, which, in order to achieve resolution, is stopped when about 50% of the theoretical amount of base required for complete hydrolysis of the ester is consumed. At this point, nearly all of the undesired S-enantiomer is hydrolyzed to acid, while nearly all of the desired R-enantiomer remains unhydrolyzed. Of course, the desired neutral ester is readily separated from the acid using conventional techniques, e.g., by extraction of the ester into an inorganic solvent at a pH where the acid is neutralized, e.g., as the water soluble sodium salt.

Further according to the present invention, the optically active ester (I) is converted by an overall novel series of steps to the aldehyde of the formula (V). While this overall process is new, the individual steps, hydride reduction of carboxylate ester to alcohol (COOR'→$CH_2OH$), trifluoromethylsulfonation ($CH_2OH$→$H_2OSO_2CF_3$) and coupling of the triflate with phenylmagnesium bromide ($CH_2OSO_2CF_3$→$CH_2C_6H_5$) are analogous to reactions known in the art. For a review of the hydride reduction of esters, see House, Modern Synthetic Reactions, 2nd Edition, W. A. Benjamin, Inc., Menlo Park Calif., 1972, pp. 71-105. For a description of the CuBr catalyzed coupling of triflate esters with Grignard reagents, see Kotsuki et al., Tetrahedron Letters, v. 30, pp. 1281-1284 (1989).

The racemic esters of the formula (I), used as starting materials are obtained from the corresponding racemic chroman-2-carboxylic acid by conventional methods of esterification. A specific method for the preparation of the ethyl ester is exemplified below. Although other methods are available in the literature, chroman-2-carboxylic acid is preferably made according to the method of Augstein et al., J. Med. Chem., v. 11, pp. 844-848 (1968).

The end product, 2R-benzylchroman-6-carbaldehyde, of the formula (V) above, is used in the synthesis of the hypoglycemic agent of the above formula (A) according to methods disclosed in Eggler et al cited above.

The present invention is illustrated by the following examples, but is not limited to the details thereof.

EXAMPLE 1

Ethyl Chroman-2-carboxylate

Chroman-2-carboxylic acid (35.6 g, 0.2 mol) prepared according to the method of Augstein et al., J. Med. Chem., v. 11, pp. 844–848, 1968) and absolute ethanol (24.3 g, 0.6 mol) were combined in 300 ml of $CH_2Cl_2$. $H_2SO_4$ (0.6 ml, 96%) was added and the mixture gently refluxed for 21 hours, then cooled and diluted with 500 ml $H_2O$. The organic layer was separated, washed with saturated $NaHCO_3$ and then $H_2O$, dried ($MgSO_4$) and stripped to yield present title product as an oil; 38.6 g (93%); $^1$H-NMR ($CDCl_3$), 300 MHz) delta 7.12 (t, 1H), 7.02 (d, 1H), 6.92 (d, 1H), 6.85 (t, 1H), 4.71 (q, 1H), 4.25 (q. 2H), 2.80 (m, 2H), 2.22 (m, 2H), 1.29 (t, 3H).

EXAMPLE 2

Ethyl 2R-Chroman-2-carboxylate

Commercial lipase, derived from *Pseudomonas fluorescens* (1.25 g) was combined with 125 ml distilled $H_2O$ and the resulting hazy solution warmed to 35° C. The pH was 7.02 as title product of the preceding Example (25.8 g, 0.125 mol) was added in a steady stream. The mixture was stirred at 35°±2° C. as the pH was maintained at 5.5–7.3 over a 7 hour period of time with 1.0N NaOH (68.7 ml, 110% of theory for 50% hydrolysis of the racemic ester). The cooled reaction mixture was extracted 2×125 ml and 1×50 ml of hexanes (emulsions were broken by filtration over diatomaceous earth), and the organic layers were combined, back washed 2×100 ml $H_2O$, dried ($MgSO_4$) and stripped to yield present title product as an oil; 11.4 g (94%); $[alpha]_D^{25} = -9.3°$ (c=1.24 $CH_3OH$).

The original aqueous layer was combined with 125 ml of ethyl acetate and the pH adjusted from 7 to 1.5 with 12N HCl. The layers were separated and the aqueous layer extracted 2×60 ml of fresh ethyl acetate. The organic layers were combined, back-washed 2×400 ml $H_2O$, dried ($MgSO_4$), stripped to a solid residue, and crystallized from 75 ml of hot hexanes to yield by-product 2S-chroman-2-carboxylic acid, 11.0 g (91%), suitable for conventional racemization and recycling to racemic ethyl ester according to Example 3 above.

EXAMPLE 3

2R-(Hydroxymethyl)chroman

Under $N_2$, title product of the preceding Example (43.3 g, 0.21 mol) was combined with tetrahydrofuran (433 mol) and $H_2O$ (44 ml). The resulting solution was stirred at 10° C.–20° C. as $NaBH_4$ (18.91 g, 0.5 mol) was added in small portions over a one hour period. The mixture was stirred overnight at 25° C., then cooled to 5° C. and 40 ml of acetone slowly added over a 30 minute period. After stirring for one hour at 10° C. to destroy excess hydride, the mixture was diluted with 750 ml $H_2O$ and then 30 ml $CH_2Cl_2$. The separated aqueous layer was extracted 2×200 ml fresh $CH_2Cl_2$. The organic layers were combined, backwashed 3×500 ml $H_2O$, dried ($MgSO_4$) and stripped to dryness to yield present title product, 32.3 g (94%); $[alpha]_D^{23} = -133.4°$ (c=1.12 $CH_3OH$); $^1$H-NMR ($CDCl_3$, 300 MHz) delta 7.05 (m, 2H), 6.83 (m, 2H), 4.15 (m, 1H), 3.8 (m, 2H), 2.85 (m, 2H), 2.24 (t, 1H), 1.79 (m, 2H).

EXAMPLE 4

(2R-Chromanyl)methyl Triflate

Under $N_2$, a solution of title product of the preceding Example (14.0 g, 0.085 mol) and pyridine (15.8 g, 0.200 mol) in 400 ml of $CH_2Cl_2$ was cooled to $-5°$ C. Triflic anhydride (28.8 g, 0.102 mol) in 50 ml of $CH_2Cl_2$ was added dropwise over 30 minutes, maintaining an internal temperature of $0°\pm5°$ C. After stirring an additional hour at $0°$ C., the reaction mixture was diluted with 200 ml $H_2O$, stirred 15 minutes, and the layers separated. The organic layer was extracted $1\times100$ ml $CH_2Cl_2$. The organic layers were combined, washed in sequence $2\times100$ ml 1N HCl, $1\times200$ ml $H_2O$, $2\times200$ ml saturated $NaHCO_3$ and $2\times200$ ml $H_2O$, dried ($MgSO_4$) and stripped to yield present title product as an oil, 23.7 g (94%); $[alpha]_D = -65.1°$ (c=1 methanol); $^1$H-NMR ($CDCl_3$, 300 MHz) delta 7.10 (m, 2H), 6.85 (m, 2H), 4.63 (m, 2H), 4.30 (m, 1H), 2.87 (m, 2H), 2.05 (m, 1H), 1.87 (m, 1H).

EXAMPLE 5

2R-Benzylchroman

Under $N_2$, title product of the preceding Example (23.2 g, 0.0783 mol) and cuprous bromide dimethylsulfide complex (2.8 g, 0.0136 mol) were combined in 326 ml of dry tetrahydrofuran and the mixture cooled to $-5°$ C. 3M Phenylmagnesium bromide in ether (71.5 ml, 0.215 mol) was added via syringe over a 20 minute period, maintaining the temperature at $0°\pm5°$ C. After stirring for 2.5 hours at $0°$ C., the reaction mixture was poured slowly into a stirred mixture of $H_2O$ (800 ml), $NH_4Cl$ (96 g, 1.8 mol) and $CH_2Cl_2$ (400 ml). The layers were separated and the aqueous layer washed $2\times200$ ml $CH_2Cl_2$. The combined organic layers were backwashed $2\times400$ ml 10% $NH_4Cl$ and then $2\times200$ ml $H_2O$, dried ($MgSO_4$) and stripped to yield present title product as an oil containing 10% biphenyl; 19.3 g (100% corrected for biphenyl content); $[alpha]_D^{25} = -96.9°$ (c=1 methanol) (uncorrected for biphenyl content). This material was suitable for use in the next step, but was optionally purified by chromatography on silica gel, eluting the biphenyl with hexane (yielding 2.21 g) and present title product with 1:9 $CH_2Cl_2$: hexane to yield 14.87 g (85%) of purified title product, $[alpha]_D = -110°$ (c=1.0, methanol); $^1$H-NMR ($CDCl_3$, 300 MHz) delta 7.29 (m, 5H), 7.08 (m, 2H), 6.85 (m, 2H), 4.24 (m, 1H), 3.08 (q, 1H), 2.89 (q, 1H), 2.77 (m, 2H), 2.00 (m, 1H), 1.73 (m, 1H).

EXAMPLE 6

2R-Benzylchroman-6-carbaldehyde

With stirring and under $N_2$, $POCl_3$ (31.74 g, 0.207 mol) was slowly added to N-methylformanilide (27.98 g, 0.207 mol). After stirring for 15 minutes, title product of the preceding Example (28.61 g, 0.138 mol; corrected for biphenyl content) was added and then 30 ml of $CH_2Cl_2$. After stirring for 15 minutes, the resulting solution was warmed in a 65° C. oil bath for one hour, as the $CH_2Cl_2$ distilled away from the mixture. The mixture was cooled to room temperature, diluted with 150 ml $CH_2Cl_2$ and poured slowly into a stirred mixture of $CH_2Cl_2$ (250 ml) and 15% (W/V) aqueous sodium acetate. After stirring for one hour, the layers were separated and the aqueous layer extracted $1\times100$ ml $CH_2Cl_2$. The combined organic layers were washed in sequence $1\times400$ ml 15% sodium acetate, $1\times250$ ml 1N HCl and $1\times250$ ml $H_2O$, dried ($MgSO_4$) and stripped to an oil (47.1 g). The oil was dissolved in 144 ml of absolute ethanol at 40° C. To the warm solution was added $NaHSO_3$ (57.5 g, 0.552 mol) in 144 ml $H_2O$ and 106 ml ethanol over 5 minutes at 40°–42° C., and the mixture stirred for one hour as it cooled to room temperature, at which point the bisulfate adduct of present title product, 39.8 g, was recovered by filtration. This was added in portions to a stirred 40° C. mixture of toluene (250 ml), $H_2O$ (400 ml) and $Na_2CO_3$ (42.3 g, 0.4 mol). After stirring and cooling to room temperature for 15 minutes, the mixture was diluted with 250 ml of hexane, stirred one hour and the layers separated. The aqueous layer was washed with 200 ml of 1:1 toluene:hexane. The organic layers were combined, extracted $1\times300$ ml $H_2O$, treated with 2 g activated carbon, dried ($MgSO_4$) and stripped to yield present title product as an oil which crystallized on standing, 27.2 g (76%). Recrystallization from hot isopropanol and hexanes gave purified title product in 2 crops, 21.0 g; mp 70°–71.5° C.; $[alpha]_D^{25} = -166°$ (c=1, methanol); $^1$H-NMR ($CDCl_3$), 300 MHz) delta 9.80 (s, 1H, CHO), 7.60 (m, 2H), 7.25 (m, 5H), 6.90 (d, 1H), 4.30 (m, 1H), 3.16 (q, 1H), 2.90 (q, 1H), 2.79 (m, 2H), 2.04 (m, 1H), 1.72 (m, 1H).

This product was previously reported by Eggler et al., U.S. Pat. No. 4,703,052, prepared by the oxidation of 2R-benzyl-6-(hydroxymethyl)chroman.

I claim:

1. An optically active compound of the absolute stereochemical formula

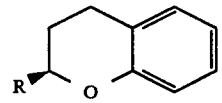

wherein R is $CH_2OSO_2CF_3$ or benzyl.

2. The compound of claim 1 wherein R is $CH_2OSO_2CF_3$.

3. The compound of claim 1 wherein R is benzyl.

* * * * *